United States Patent [19]
Urata et al.

[11] Patent Number: 5,514,341
[45] Date of Patent: May 7, 1996

[54] FECES-SAMPLING TRANSPORT CONTAINER

[75] Inventors: Takeyoshi Urata, Hasuda; Hiromi Urano, Kitakatsushika; Shinichiro Asano, Kamagaya; Tatsunori Kikuchi, Kuki; Shigeru Aota, Yokohama; Hiroaki Hayashi, Konosu; Yoshiharu Ichikawa, Tokyo, all of Japan

[73] Assignee: Eiken Kagaku Kabushiki Kaisha, Tokyo, Japan

[21] Appl. No.: 290,892

[22] PCT Filed: Dec. 17, 1993

[86] PCT No.: PCT/JP93/01833

§ 371 Date: Sep. 20, 1994

§ 102(e) Date: Sep. 20, 1994

[87] PCT Pub. No.: WO94/15212

PCT Pub. Date: Jul. 7, 1994

[30] Foreign Application Priority Data

Dec. 18, 1992 [JP] Japan ............... 4-355816
Jun. 22, 1993 [JP] Japan ............... 5-173566
Aug. 30, 1993 [JP] Japan ............... 5-235853

[51] Int. Cl.⁶ .......................... G01N 33/48; G01N 33/50
[52] U.S. Cl. .......................... 422/102; 422/58; 422/61; 73/864.41; 128/757; 436/66; 436/518
[58] Field of Search .................. 422/58, 61, 99–102, 422/104; 73/864.41; 128/757; 436/66, 518; 210/232, 445, 927; 604/406

[56] References Cited

U.S. PATENT DOCUMENTS

| | | | |
|---|---|---|---|
| 3,421,858 | 1/1969 | Quinn | 422/103 |
| 3,640,268 | 2/1972 | Davis | 128/757 X |
| 3,732,981 | 5/1973 | Mendelsohn | 210/94 |
| 4,066,646 | 1/1978 | LeBlanc et al. | 422/102 |
| 4,148,732 | 4/1979 | Burrow et al. | 210/232 |
| 4,426,295 | 1/1984 | Evans et al. | 210/772 |
| 4,453,927 | 6/1984 | Sinko | 604/52 |
| 4,578,245 | 3/1986 | Arai et al. | 422/56 |
| 4,859,610 | 8/1989 | Maggio | 436/518 |
| 4,889,256 | 12/1989 | Fowles | 220/306 |
| 5,149,506 | 9/1992 | Skiba et al. | 422/102 |
| 5,246,669 | 9/1993 | Hayashi | 422/101 |
| 5,286,454 | 2/1994 | Nilsson et al. | 422/102 |

FOREIGN PATENT DOCUMENTS

| | | |
|---|---|---|
| 0175326 | 3/1986 | European Pat. Off. . |
| 59-125064 | 7/1984 | Japan . |
| 62-69160 | 4/1987 | Japan . |
| 64-42454 | 3/1989 | Japan . |
| 2-140468 | 11/1990 | Japan . |
| 4140635 | 5/1992 | Japan . |
| 4-140635 | 5/1992 | Japan . |
| 5034340 | 2/1993 | Japan . |
| 5-34340 | 2/1993 | Japan . |
| 5093722 | 4/1993 | Japan . |
| 5-93722 | 4/1993 | Japan . |
| 5027671 | 4/1993 | Japan . |
| 5-27671 | 7/1993 | Japan . |
| 5296997 | 11/1993 | Japan . |

*Primary Examiner*—Jill Warden
*Assistant Examiner*—Harold Y. Pyon
*Attorney, Agent, or Firm*—Oliff & Berridge

[57] ABSTRACT

A feces-sampling transport container includes a cylindrical container body capable of accommodating a liquid; a cap equipped with a sampling rod; a separating wall disposed in the container body; a filter for filtering a liquid; and a dropping portion for the filtered liquid. The filter has its outer circumferential portions clamped and fixed by a stepped portion in the container body and the end face of the dropping portion. In this container, the filter has a high effective filtration area percentage. Moreover, the container is so easily transported that it can be sent and/or returned by via mail such as by packaging it in an envelope. Thus, the container has a high usability.

28 Claims, 12 Drawing Sheets

FECES-SAMPLING TRANSPORT CONTAINER

TECHNICAL FIELD

The present invention relates to a feces-sampling transport container and, more particularly, to an easily transportable feces-sampling container capable of being sent and/or returned by means of mail such as by packaging it in an envelope.

BACKGROUND ART

The feces is suitable like urine as a non-invasive examination sample so that it is broadly used as the sample in several examinations.

Of the aforementioned examinations, the detection of occult blood in the feces is known as the screening method of a digestive disease such as a discharge of blood from a digestive tract and is very important for diagnosis of a hemorrhagic disease such as an ulcer or cancer of the digestive tract.

In the method of detecting the occult blood in the feces, the method (e.g., Japanese Patent Laid-Open No. 125064/1984) based upon the immunological reaction principle, as recently reported, is superior in the points of specificity and sensitivity to the conventional detection method using the guaiac reagent and is noted as a new screening method for the aforementioned disease.

Incidentally, in order to execute the method of detecting the occult blood in the feces on the basis of the immunological reaction principle, it is necessary to sample the feces quantitatively in advance and to suspend the sampled feces in a suitable liquid thereby to prepare a predetermined feces suspension.

This is because the immunological detection reagent is preset to achieve a sensitivity according to a specimen to be anticipated, i.e., the amount of the feces, so that the sensitivity is lowered if the amount of the feces to be examined is too small. On the contrary, too much feces to be examined will cause inconveniences for the transportation or mailing and emit an offensive odor. Moreover, a problem will arise when an excess of the specimen (i.e., the feces) is to be disposed after the examination.

In order to eliminate these difficulties, there have been proposed in the prior art a variety of feces-sampling transport containers. For example, Japanese Utility Model Laid-Open No. 69160/1987 has disclosed a feces-sampling transport container which is equipped with a sampling rod having a notched portion, a recessed portion or a through hole in the vicinity of its leading end.

When the feces-sampling transport container disclosed in Japanese Utility Model Laid-Open No. 69160/1987 is used, a substantially constant amount of feces sample is held in the notched portion, the recessed portion or the through hole formed in the vicinity of the leading end of the sampling rod, so that the amount of feces to be sampled can be limited to a certain extent. It is, however, limitative to control the amount of feces to be sampled, exclusively by the leading end structure of the sampling rod. Depending upon the physical properties of the feces, for example, the sampling amount may get excessive or short.

The feces-sampling transport container having succeeded in eliminating the difficulties of the feces-sampling transport container disclosed in Japanese Utility Model Laid-Open No. 69160/1987 is exemplified by the feces-sampling transport container which is disclosed in Japanese Utility Model Laid-Open No. 42454/1989, as shown in FIG. 18. This feces-sampling transport container is constructed to include: a container body 2 capable of accommodating a liquid 1 for suspending feces; a cap 4 equipped with a sampling rod 3 having at least one of a notched portion, a recessed portion and a through hole in the vicinity of its leading end and capable of being connected to the container body 2 through sealable means; and a dropping portion 6 having a filter 5 therein. The feces-sampling transport container is provided with a stocker portion 8 which is formed by the cap 4, a separating wall 7 for separating the inside of the container into at least two chambers, and the sampling rod 3 extending through the separating wall 7. In FIG. 18, other reference numerals 9 and 10 designate a hole and a notched portion.

In the feces-sampling transport container shown in FIG. 18, the sampling rod 3 is inserted into the feces to be examined to sample a certain amount of feces at its leading end portion. After this, the sampling rod 3 is inserted through the hole 9 of the separating wall 7 into the container body 2. At this time, an excess of feces can be rubbed out by the hole 9. As a result, a constant amount of feces sample can be easily sampled at the notched portion 10.

In the transportation of the feces-sampling transport container, on the other hand, it would be practically convenient to send and/or return the feces-sampling transport container by means of (regular) mailing envelopes. In the case of transportation by the mailing envelope, however, there are usually some limits. According to the Japanese regulations, for example, the thickness of the envelope must not exceed 10 mm. In the feces-sampling transport container disclosed in Japanese Utility Model Laid-Open No. A2454/1989 and shown in FIG. 18, however, the container body 2 is not slender but has a larger diameter than 10 mm. Thus, there arises a difficulty that the feces-sampling transport container cannot be sent and or returned in Japan by the (regular) malling envelope.

The feces-sampling transport container having succeeded in eliminating the difficulty of the feces-sampling transport container disclosed in Japanese Utility Model Laid-Open No. 42454/1989 is exemplified by the feces-sampling transport container disclosed in Japanese Utility Model Laid-Open No. 140468/1990 and shown in FIG. 19. According to this disclosure, in the feces-sampling transport container, a container body 12 charged with a liquid 11 is equipped with a dropping portion 13 at its leading end and has its leading end sealed with a cap 14, and this cap 14 is equipped with a sampling rod 15 to be inserted into the container body 12. This container body 12 is molded into a slender shape, in which is fixed a rubber plug 17 dividing the container body 12 into two chambers and having a hole 16 receiving the sampling rod 15 in a manner to slide on its outer circumference. The cap 14 is press-fitted in the container body 12 through an O-ring 18. The sampling rod 15 is formed with a helical groove 19 at its leading end. The dropping portion 13 is equipped therein with a malt filter 20 and a filter 21.

In addition to the aforementioned feces-sampling transport container, there has been proposed a feces-sampling transport container having a filter, as disclosed in EP-175326 or U.S. Pat. No. 5,246,669.

The feces-sampling transport container, as disclosed in Japanese Utility Model Laid-Open No. 140468/1990, can be sent and/or returned in Japan by means of the (regular) mailing envelope because its container body 12 has an external diameter of about 9 mm. Since, however, the container body 12 is molded in an elongated slender shape, the dropping portion 13 has its leading end portion so reduced in the external diameter that it cannot retain a sufficiently large filtration area (or effective diameter) for the malt filter 20 and the filter 21.

Incidentally, some specimen or feces contains fine particle or a mucus called the mucin. This feces is called the "hard-extraction feces" or "hard-filtration feces" because it is hard to filter when a predetermined amount of specimen is to be extracted for the examination through the filter from its suspension in the aforementioned container.

For the examination of the feces, it is usually necessary to extract four droplets of the specimen through the filter from that suspension. Since there may arise a failure of sampling the specimen droplets or a re-examination, it is preferable to extract some excess of the specimen droplets. According to the aforementioned feces-sampling transport containers disclosed in Japanese Utility Model Laid-open Nos. 42454/1989 and 140468/1990, however, the specimen is hard to extract in a sufficient amount for the examination in case it is the hard-extraction feces or the hard-filtration feces.

The feces-sampling transport container disclosed in EP-175326 belongs to that having the filter at an early stage. Thus, this feccs-sampling transport container does not have any quantitative feces sampling mechanism but has a large container body so that it is not suited for transportation, especially for mailing.

On the other hand, the feces-sampling transport container disclosed in U.S. Pat. No. 5,246,669 is of the new type equipped with the quantitatively feces sampling mechanism. This feccs-sampling transport container is equipped with a mechanism for preventing any pressure rise in the container body when the feces sampling rod is inserted into the container body. However, the disclosure of U.S. Pat. No. 5,246,669 has failed to investigate or hint any solution to the largest problem to be caused in case the feces-sampling transport container is thinned to achieve convenience for transportation or mailing, namely, the problem that the effective filtration area of the filter is not retained so that a sufficient filtered liquid cannot be achieved.

The present invention has been conceived to solve the above-specified problems of the prior art and has an object to provide a feccs-sampling transport container which can have such a convenient usability as to sample a proper amount of feces specimen easily, which is so convenient in transportation that it can be easily sent and/or returned by mailing means such as the envelope means, and which can easily extract a sufficient amount of specimen in a droplet form for the examination from a suspension of feces through a filter no matter what properties the feces might have.

DISCLOSURE OF THE INVENTION

According to a first aspect: 1), there is provided a feces-sampling transport container comprising: a cylindrical container body capable of accommodating a liquid for suspending feces; a cap including a sampling rod equipped at its leading end portion with feces sampling means for sampling the feces and adapted to be inserted in the axial direction into said container body, said cap being capable of sealing one end portion of said container body; a separating wall formed in said container body for partitioning the inside of said container body and for removing an excess of the feces when said sampling rod is inserted; a filter disposed in the vicinity of the other end portion of said container body for filtering the suspension of the feces; and a dropping portion fitted in the other end portion of said container body outside of said filter for dropping the liquid filtered by said filter.

wherein said container body is formed on the inner wall face of its other end portion with a stepped portion for retaining said filter, so that said filter is fixed by having its two end faces sandwiched at their outer circumferences between said stepped portion and the end face of said dropping portion.

The following modes can be enumerated as the preferred ones of the present invention:

2) A feces-sampling transport container as set forth in 1), wherein said stepped portion is formed by enlarging the internal diameter of said container body;

3) A feces-sampling transport container as set forth in 1), wherein said stepped portion is formed by reducing the internal diameter of said container body;

4) A feces-sampling transport container as set forth in 3), wherein said container body has its internal diameter reduced by means of a stopper ring;

5) A feces-sampling transport container as set forth in 1), wherein said filter is an aseptic filter;

6) A feces-sampling transport container as set forth in 1), wherein said filter is formed by laminating at least two kinds of filters;

7) A feces-sampling transport container as set forth in 1), wherein the face of said filter to abut against said stepped portion bulges toward said cap from said stepped portion;

8) A feces-sampling transport container as set forth in 1), further comprising a filter disposed in the passage which is formed below in said dropping portion for the filtered liquid;

9) A feces-sampling transport container as set forth in 1), wherein said dropping portion has a flange extended outward from the outer circumference of said container body for preventing said feces-sampling transport container from rolling;

10) A feces-sampling transport container as set forth in 1), wherein said cap is flanked or knurled outward from the outer circumference of said container body for preventing said feces-sampling transport container from rolling;

11) A feces-sampling transport container as set forth in 1), wherein said container body has its inner wall face treated physically/chemically to improve its wettability;

12) A feces-sampling transport container as set forth in 11), wherein said physical/chemical treatment is a physical treatment;

13) A feces-sampling transport container as set forth in 12), wherein said physical treatment is carried out by a corona discharge;

14) A feces-sampling transport container as set forth in 11), wherein said physical/chemical treatment is a chemical treatment;

15) A feces-sampling transport container as set forth in 14), wherein said chemical treatment is carried out with lithium hydroxide;

16) A feces-sampling transport container as set forth in 1), wherein said container body contains an anti-fogging agent for improving the wettability of the inner wall face of said container body;

17) A feces-sampling transport container as set forth in 1), wherein said separating wall is formed into a cylindrical shape having a through hole at its central portion for inserting said sampling rod, by protruding the inner wall face of said container body inward;

18) A feces-sampling transport container as set forth in 17), wherein said through hole has its inner wall face formed at its portion into an inward bulging ring portion whereas said sampling rod is formed a recessed ring portion at its portion corresponding said bulging ring portion;

19) A feces-sampling transport container as set forth in 1), wherein said separating wall is formed on its circumference with a feces rubbing-off ridge for engaging hermetically with the circumference of said sampling rod, and wherein said sampling rod has its circumference formed in at least its portion with a recess which is made axially longer than the ridge of said separating wall and confronts said separating wall, whereby communication is provided between those spaces in said container body, which are partitioned by said separating wall, to reduce the pressure in said container body to the atmospheric level before said sampling rod is inserted to a predetermined position in said container body;

20) A feces-sampling transport container as set forth in 19), wherein said ridge is formed in the vicinity of the free end portion of said separating wall;

21) A feces-sampling transport container as set forth in 19), wherein the recess formed in the circumference of said sampling rod is a notched groove formed in a portion of the circumference of said sampling rod;

22) A feces-sampling transport container as set forth in 19), wherein the recess formed in the circumference of said sampling rod is formed into a radially reduced portion by notching the circumference of said sampling rod in its entirety;

23) A feces-sampling transport container as set forth in 1), further comprising a ring-shaped stopper member fitted in said container body inside of said filter and in contact with the filtering face of said filter for clamping and fixing said filter between itself and said dropping portion, wherein said ring-shaped stopper member includes an inlet portion having an upper open end communicating with the inside of said cylindrical container body and a lower open end to contact with the filtering face of said filter, such that said inlet portion has its radial section area increased gradually from said upper open end to said lower open end, and wherein a depositing portion for separating/settling at least a portion of the solid substances in the suspension of the feces is formed between the outer circumferential wall of said ring-shaped stopper member and the inner circumferential wall of said cylindrical container body;

24) A feces-sampling transport container as set forth in 23), wherein said stopper member has its circumferential wall formed with radially opened inlet holes for providing communication between the inlet portion thereof and said depositing portion;

25) A feces-sampling transport container as set forth in 23), wherein said stopper member is formed at the edge portion of said upper open end with tooth-shaped cut-away portions opened in the radial direction to act as inlet holes;

26) A feces-sampling transport container as set forth in 23), wherein said stopper member has its upper open end closed and formed in the circumferential wall in the vicinity of its upper end portion with a multiplicity of radially opened through holes as inlet holes;

27) A feces-sampling transport container as set forth in 23), wherein the sectional area ratio of the upper open end of said stopper member, as taken in the radial direction, to the lower open end is no more than $1/3$; and 28) A feces-sampling transport container as set forth in 23), wherein the surface area of that portion of the surface of said filter opposed to said dropping portion, which contacts with the inside space of said container body, is at least 50% or more than the maximum of the sectional area of said container body, as taken normal to the axial direction.

The container body of the feces-sampling transport container of the present invention should not have its shape limited to any special one such as a circular or square cylinder, if it has a capacity capable of accommodating a liquid in an amount necessary for suspending the feces in a desired concentration, and if it has a length having no obstruction against the sampling rod which is fixed in the cap, when the cap is fitted in the container body. Moreover, the size of the container body preferably its maximum diameter reduced (or thinned) to such a range (e.g., 10 mm or less) as to achieve the using object of the container, and this maximum diameter is suitably selected to make the transportation convenient.

The transportation means may be exemplified by such one as can be easily and inexpensively used by anyone. Specifically, the transportation may preferably be exemplified by sending and/or returning the container by mailing means such as a mailing envelope (preferably of a regular size). Hence, the container body may have its maximum diameter made smaller than that which is allowed by the mailing regulations of Japan for the feces-sampling transport container of the present invention.

The container body can be made of a synthetic resin such as polyethylene, polypropylene or polyvinyl chloride. Especially if a soft material such as polyethylene or polypropylene is used, it is convenient because the feces suspension is easily expelled out of the container body.

The sampling rod of the cap should not have its shape limited to anything special, if it is equipped in the vicinity of its leading end with feces sampling means such as any of the notched portion, the recessed portion or the through hole. Moreover, the sampling rod can be made of any material such as synthetic resin, glass, metal or ceramics, if this material is made so hard as to be easily pierced into the feces. In order to form a hermetical rubbing face between the sampling rod and the separating wall of the aforementioned container body, however, it is preferable to use the aforementioned various materials is making the container body.

The means to be mounted in the container body and/or the cap for sealing one end portion of the container body with the cap can be exemplified by the screwing or fitting one which is currently used. Moreover, the sampling rod to be attached to the cap may preferably be formed with the stopper member which can engage with the separating wall in the position where the cap is completely screwed or fitted in the container body.

The liquid for suspending the feces may be exemplified by an arbitrary one such as psychologic saline solution or a buffer solution which may contain various buffers, if it can achieve the intrinsic object. Moreover, an additive such as a dyestuff, antiseptic agent, deodorant or stabilizer can be added, if necessary, to the liquid unless it adversely affects the analysis results.

The buffer used may be any for holding the pH in the neutral range and is exemplified by HEPES, PIPES, TES or MOPS, and the pH value is selected by considering the stability of the component to be analyzed. An isotonic solution can be prepared by adding NaCl to a concentration of 0.9%. In case the object to be examined is the occult blood, a protein such as bovine serum albumin, ovalbumin or egg-white albumin is added as the stabilizer. The amount of use is preferably about 0.1 to 10 % w/v.

The amount of liquid to be confined in the container body is prepared according to the desired suspension concentration of the feces. In case 5 mg of feces is to be sampled by the sampling portion of the sampling rod, for example, a degree of dilution of 400 times can be achieved by setting the liquid to 2 ml.

The separating wall may be formed by projecting the inner wall face of the container body inward or exemplified by another member such as a rubber plug having predetermined properties.

The dropping portion is so suitably prepared by having its leading end portion pierced by suitable piercing means or cut as to satisfy the condition that the feces suspension can be dropped through the filter when the dropping portion is formed, thus, the dropping portion conveniently has its leading end face thinned to facilitate the piercing operation. The dropping portion can be pierced with the hole, as described above, or can have its projecting portion flawed so that it may be folded at the flaw.

The method of enlarging the internal diameter of the container body at the stepped portion which is formed on the inner wall face of the other end portion of the container body for retaining the filter is specifically exemplified by thinning the container body or by enlarging the external diameter while leaving the thickness of the container body as it is.

The method of reducing the internal diameter of the container body at the stepped portion which is formed on the inner wall face of the other end portion of the container body for retaining the filter is specifically exemplified by thickening the container body partially (e.g. by forming a bulging portion) or by fitting another member such as the stopper ring in the container body while leaving the thickness of the container body as it is.

Since the filter to be used in the feces-sampling transport container of the present invention is provided for filtering out the undigested solid content which will obstruct the examinations, it may be inactive to the substances to be analyzed but its material should not be limited. This material can be specifically exemplified by a porous substance such as polyurethane sponge or filter paper or by a fibrous substance such as glass wool or absorbent wadding. The filter may more preferably be exemplified by an aseptic filtration filter such as a glass wool filter or a membrane filter having a predetermined pore diameter.

Moreover, the filter described above may be composed of one kind of filter or formed by laminating two or more kinds of filters.

Still moreover, the filtering face of the filter, at which the filter contacts with the aforementioned stepped portion, may be flat but may more preferably bulge from the stepped portion toward the aforementioned cap to increase the effective filtration area. The shape of the bulging portion of the filter of this case may be exemplified by one or more semispherical, semi-elliptic, conical or pyramidal shapes.

In the aforementioned filtered passage in the dropping portion, there may be disposed another filter. This filter is positioned so as to filter the feces suspension reliably when the suspension is to be dropped from the dropping portion pierced in the leading end of the dropping portion. This additional filter can perform not only the filtering function but also a function as the member for supporting the intrinsic filter in the container body.

This container body is preferably made cylindrical from the standpoints of strength and feasibility of manufacture but is then liable to roll. In order to prevent this rolling motion of the feces-sampling transport container, the aforementioned dropping portion may be formed with the flange which protrudes outward from the outer circumference of the container body. The shape of this flange may be determined to prevent the rolling motion of the feces-sampling transport container but should not be limited, and may be exemplified by a square, pentagonal, hexagonal or star shape, or their modification such as a chamfered shape.

Moreover, the aforementioned cap may be flanged, as described above, or knurled. Still moreover, the rolling preventing shape may be formed at both the dropping portion and the cap.

Since the aforementioned container body is shaped to have a considerable length, its inner wall face fails to be wetted with a liquid for suspending the feces, if it is water-repellent, so that the liquid resides in a portion and fails to be entirely agitated. In order to improve the wettability, therefore, the inner wall face may be subjected to a physical/chemical treatment, or the container body may be made of a material containing an anti-fogging agent.

The physical/chemical treatment is further divided into a physical treatment and a chemical treatment. One of these treatments is usually carried out, but both may be carried out together.

The physical treatment may be exemplified by a treatment with a corona discharge. The condition for this corona discharge treatment is suitably selected for an optimum wettability.

The chemical treatment may be exemplified by a treatment with a suitable chemical agent such as lithium hydroxide. The condition for this treatment with lithium hydroxide is suitably selected for optimum wettability.

The anti-fogging agent to be mixed into the material of the container body is exemplified by a surface active agent composed of: fatty acid ester such as monoglycerlde fatty acid ester, sorbitan fatty acid ester, propylene glycol fatty acid ester or higher alcohol fatty acid ester; an ethylene oxide additive such as polyoxyethylene alkyl ether or polyoxyethylene sorbitan fatty acid ester; or their mixture. Moreover, the anti-fogging agent may be exemplified by a mixture which is prepared by adding an amide lubricant or a silica lubricant, if necessary, to the aforementioned surface active agent. The anti-fogging agent and the container body material can be mixed in advance before the molding of the container body by an arbitrary method such as a dry blending, a molten blending or a master batch blending.

The aforementioned container body and separating wall can conveniently be integrally formed if the container body has its inner wall face protruded inward and if the separating wall is made cylindrical to have its central portion formed with the through hole for receiving the aforementioned sampling rod.

In this case, the through hole has its inner wall face protruded inward to form a bulging ring shape, and the portion of the sampling rod corresponding to the bulging ring portion is formed with a recessed ring shape such that the bulging ring shape and the recessed ring shape abut against each other. Then, the interference between the through hole or the rubbing-out portion of the sampling rod and the sampling rod can be sufficiently retained and prevented from vanishing due to the aging.

If the feces-sampling transport container of the present invention used is constructed such that the separating wall has its circumference formed with a feces rubbing-off ridge to hermetically engage with the circumference of the sampling rod whereas the sampling rod has at least its circumferential portion formed with a recess having a larger axial length than that of the ridge of the separating wall and confronting the separating wall, the air in the container body can preferably be released to prevent the pressure rise in the container body when the sampling rod is inserted into the container body. This air vent function can be exemplified not only by that structure but also by the structure which is disclosed in U.S. Pat. No. 5,246,669.

When the feces-sampling transport container thus constructed is to be used, the feces is sampled by the leading end of the sampling rod integrated with the cap. After this, the leading end portion is inserted into the container body. The feces caught on the circumference of the leading end of the sampling rod is scraped off, while the sampling rod is passing through the separating wall, so that a predetermined amount of feces left in the helical groove is suspended in the liquid in the container body to provide the specimen to be examined. This feces-sampling transport container can be transported (or mailed) while sealing the suspension, as described above. At the examination time, the dropping portion has its thinned portion pierced to drop the suspension to the outside through the filter.

In the feces-sampling transport container thus constructed, the sampling rod is inserted while having its circumference hermetically engaging with the feces scraping ridge which is formed on the cylindrical circumference of the aforementioned separating wall. In tills case, the sliding contact between those two members occurs only at the crest of the aforementioned ridge. As a result, the sliding resistance between them is remarkably low so that the sampling rod is inserted into the container body while smoothly rubbing out the feces with a light dragging force. Even with the small contacting area between the ridge of the separating wall and the circumference of the sampling rod, moreover, the engagement with the outer circumference of the sampling rod can be enhanced during the sliding motion by the reaction of the separating wall which is being radially pushed by the ridge, to improve the sealing properties.

In the aforementioned feces-sampling transport container, moreover, when the sampling rod passes over the separating wall, the recess formed in the circumference of the sampling rod comes, immediately before it is inserted to a predetermined position, to confront the ridge formed on the separating wall of the container body. Since, the recess is made axially longer than the ridge, the spaces in the container body, as partitioned by the separating wall, are allowed to communicate with each other through the gap which is established between the recess in the circumference of the sampling rod and the circumference of the separating wall. At this instant, the container body has its inside vented to the atmosphere to acquire the atmospheric state. As a result, the pressure in the container body is held substantially at the atmospheric level even when the sampling rod is further inserted slightly to the predetermined position in the container body to establish a hermetical seal between itself and the separating wall. In short, the recess formed in the sampling rod functions as an air vent to hold the inside of the container body under the atmospheric pressure, when the sampling rod is inserted into the container body, so that the liquid can be prevented from being splashed from the dropping portion to blot the outside by the pressure, if any, simultaneously as the dropping portion is pierced for the examination. If the container body is made slender, the internal space has its capacity reduced to increase the influence of the pressure rise, as exerted when the sampling rod is inserted. Thus, without such air vent mechanism, there may arise a trouble that the content is injected at the piercing time.

Incidentally, the ridge to be formed on the separating wall may preferably be formed as close to the free end portion of the separating wall as possible, so that it may exert a more intensive reaction upon the outer circumference of the sampling rod to improve the sealing properties when it comes into sliding engagement with the sampling rod.

The recess to be axially formed in the circumference of the sampling rod may preferably have a larger length than the entire axial length of the separating wall.

The recess thus far described may be formed by cutting out the circumference of the sampling rod partially in parallel with the remaining large-diameter portion. Moreover, the recess may also be made by cutting out the circumference of the sampling rod by a predetermined axial length over the entire circumference to form a radially reduced portion. In either case, the stepped portion, at which the axial end portion of the cut-away groove or the radially reduced portion of the sampling rod and the intrinsic outer circumference are adjacent to each other, may preferably be tapered to soften the abutment between the recess and the separating wall when the sampling rod is inserted.

The feces-sampling transport container used in the present invention is constructed to comprise a spring-shaped stopper member fitted in the container body inside of the filter and in contact with the filtering face of the filter for clamping and fixing the filter between itself and the dropping portion. The ring-shaped stopper member includes an inlet portion having an upper open end communicating with the inside of the cylindrical container body and a lower open end to contact with the filtering face of the filter, such that the inlet portion has its radial section area increased gradually from the upper open end to the lower open end. A depositing portion for separating/settling at least a portion of the solid substances in the suspension of the feces is formed between the outer circumferential wall of the ring-shaped stopper member and the inner circumferential wall of the cylindrical container body. Thus, the filtering face can preferably be prevented from being clogged with the solid substances in the feces, thereby to stabilize the dropping amount of the filtered liquid.

When the feces-sampling transport container thus constructed is to be used, the feces is sampled at the lower leading end of the sampling rod made integral with the cap, and this leading end portion is then inserted into the container body. The feces thus caught on the circumference of the leading end of the sampling rod is rubbed out while the sampling rod is passing through the separating wall, so that a predetermined amount of feces left in the helical groove is suspended in the sealed liquid of the container body, to provide the specimen to be examined. The feces-sampling transport container thus prepared can be transported (or mailed) with the sealed suspension. At the examination time, the suspension is dropped to the outside through the filter by piercing the thinned portion of the dropping portion.

In the aforementioned feces-sampling transport container, the feces caught in the groove of the sampling rod is dissolved and dispersed into the suspension medium in the container body. In this case, the solid substances in the feces are settled in the liquid individually at the inlet portion, which is formed in the central hole of the ring-shaped stopper member, and at the depositing portion which is formed between the outer circumferential wall of the stopper member and the inner circumferential wall of the container body.

Since, in the feces-sampling transport container, the inlet portion of the stopper member has its radially sectional effective area enlarged gradually from the upper open end to the lower open end contacting with the filtering face (that is, the depositing portion has its radially sectional area made larger at its upper portion than at its lower portion), the amount of the dispersed solid substances to settle in the inlet portion relatively decreases. In case, on the other hand, the dispersed solid substances in the suspension are introduced into the inlet portion of the stopper member and are left at rest for a long time period, the solid substances to be deposited on the filtering face are deposited over a wide range due to that radial expansion ratio so that the thickness (or height) of the same amount of solid substances to be deposited on the filtering face is further reduced.

When the container body in this state is squeezed for examining the feces, the internal suspension is dropped out of the dropping portion from the inlet portion of the stopper member through the filter.

By the succeeding further squeezing action of the container body, the suspension in the container body above the inlet portion and above the depositing portion is introduced into the inlet portion. Since, in this case, the solid substances have already been separated from the suspension in those portions while the container body was left to stand, their filtering efficiency through the filter is not lowered.

As a result, the feces-sampling transport container has little deposition of the solid substances on the filtering face so that the filtering efficiency of the dropping suspension at the time of analyzing the sampled specimen is improved. At the same time, no large dispersion of the amount of droplets is caused by the properties of the specimen so that the analysis can be carried out in a stable sensitivity.

Incidentally, in a preferred mode of the aforementioned feces-sampling transport container, the sectional area of the upper open end of the inlet portion of the ring-shaped stopper member, as taken in the radial direction, is set to ⅓ or less than that of the lower open end, and the annular circumferential wall is formed with the radial inlet holes for providing the communication between the inlet portion and the depositing portion.

In this mode, the suspension can be introduced continuously from the inlet holes into the inlet portion even in case the upper open end of the inlet portion is clogged with a solid substance of large size before the container body is completely squeezed to the last. In this mode, moreover, the solid substances will partially enter the inlet portion through the radial inlet holes while they are dispersed into the suspension. However, the solid substances having relatively large specific gravities will settle as they are in the depositing portion around the stopper member, without substantial diffusion in the horizontal direction while they are settling. As a result, the solid/liquid separation of some extent has already been caused at the suspension preparing time, to further reduce the amount of the solid substances. This effect becomes more prominent in the mode in which the upper open end has its top completely closed while leaving only the aforementioned radial inlet holes.

The feces-sampling transport container of the present invention is most preferably modified such that the surface of the filter opposed to the dropping portion but contacting with the internal space of the container body has an area of at least 50% or more than the maximum of the sectional area of the container body, as taken in the direction normal to the axis.

Specifically, the structure of the feces-sampling container of the prior art is so restricted that the aforementioned surface area (i.e., the effective filtering area) of the filter is 30 to 40% of the maximum of the aforementioned sectional area of the container body. In the feces-sampling transport container of the present invention, however, the effective filtering area percentage of the filter can be raised to 50% or more by adopting the aforementioned construction. Thanks to this effective filtering area percentage of 50% or more, a high filtering efficiency can be realized even in case the container body is made slender.

In case a filter having a small mesh is adopted to prepare such a filtered liquid as can appear transparent by a visual observation, for example, the filter is liable to be clogged unless the filter retains an effective filtering area percentage as high as possible. In the feces-sampling transport container of the present invention, the filter is reluctant to clog even if the container body is made slender.

In the feces-sampling transport container of the present invention, the other end portion of the container body is formed on its inner wall face with the stepped portion for retaining the filter so that the filter is fixed by having its two end faces clamped at their outer circumferential portions between the stepped portion and the end face of the dropping portion. As a result, the filter used can have a large effective filtering area having a diameter substantially equal to the internal diameter of the container body.

In another preferable mode of the present invention, it is possible to provide an easy-handling feces-sampling transport container which is excellent in the operating properties and in the sealing properties at the sampling time and which is enabled to prevent the suspension from being injected or scattered even by the operations for the examinations.

In still another preferable mode of the present invention, it is possible to provide a feces-sampling transport container which can prepare a predetermined amount of filtered liquid at all times thereby to achieve a stable analyzing sensitivity because the filtering efficiency of the filter is hardly deteriorated independently of the properties of the feces specimen by the deposition of solid substances on the filtering face when the suspension of the specimen confined in the container body is to be filtered and dropped.

Figure 9:
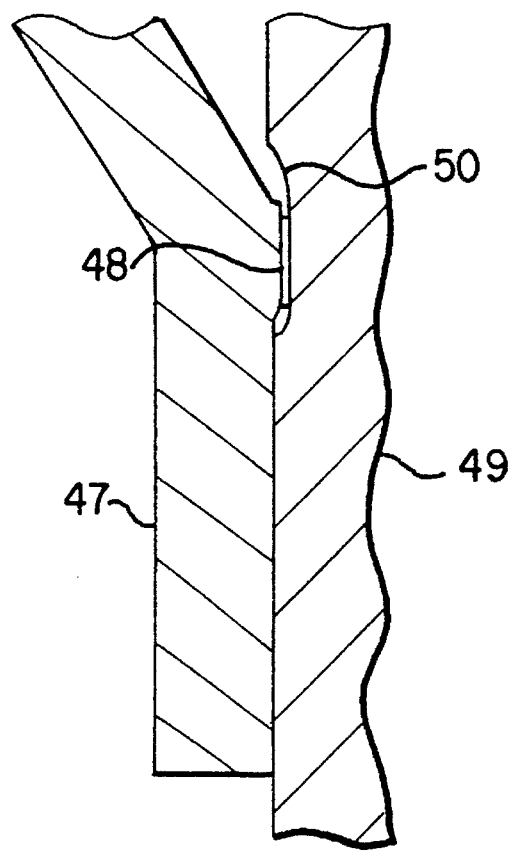
Figure 10:
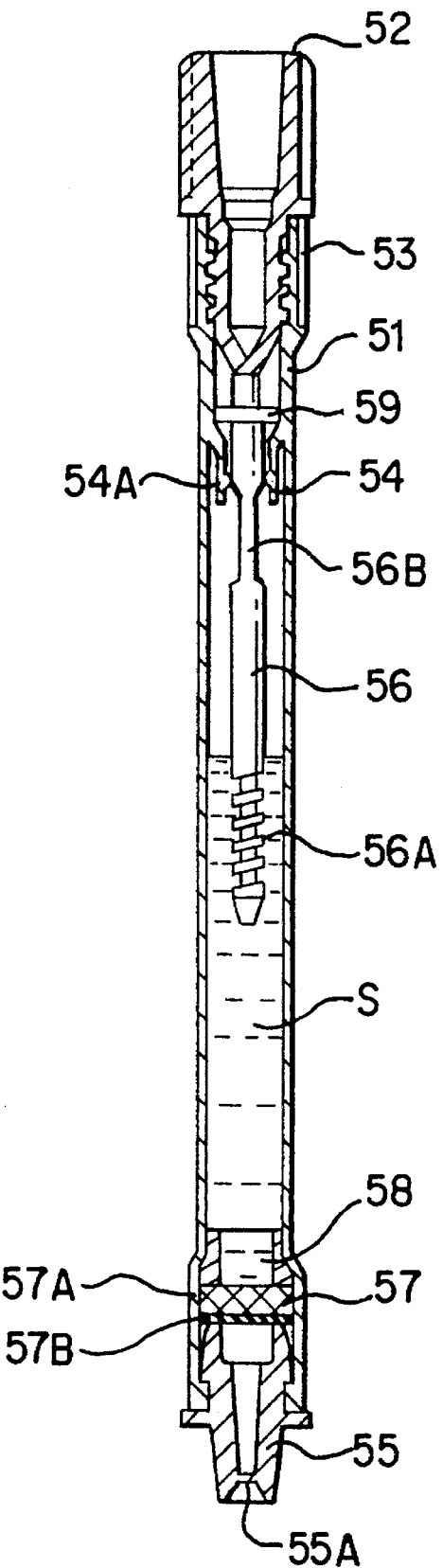
Figure 11:
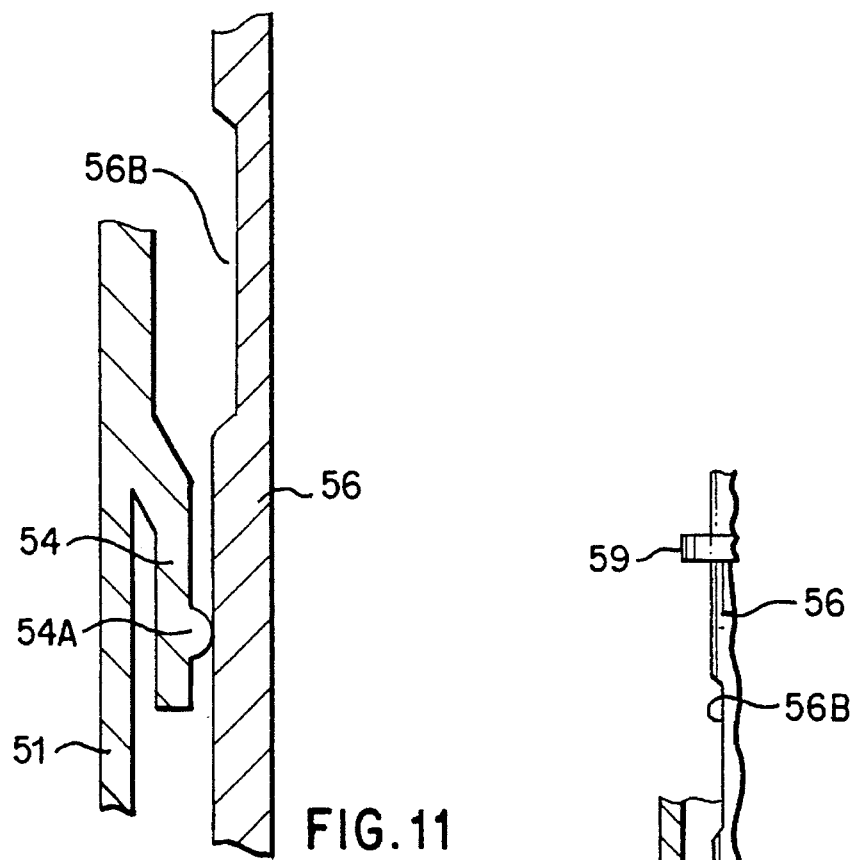
Figure 12:
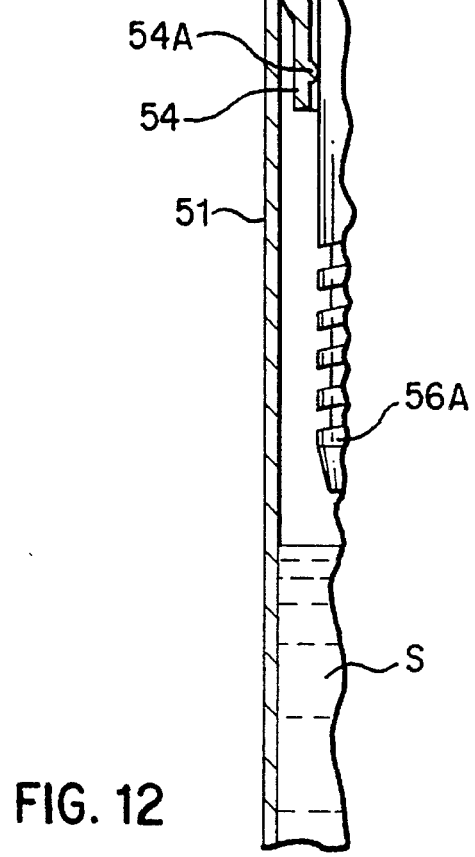
Figure 13:
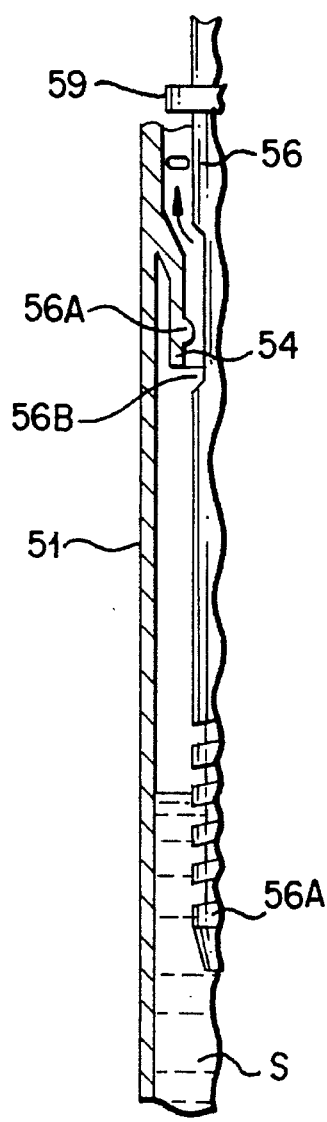
Figure 14:
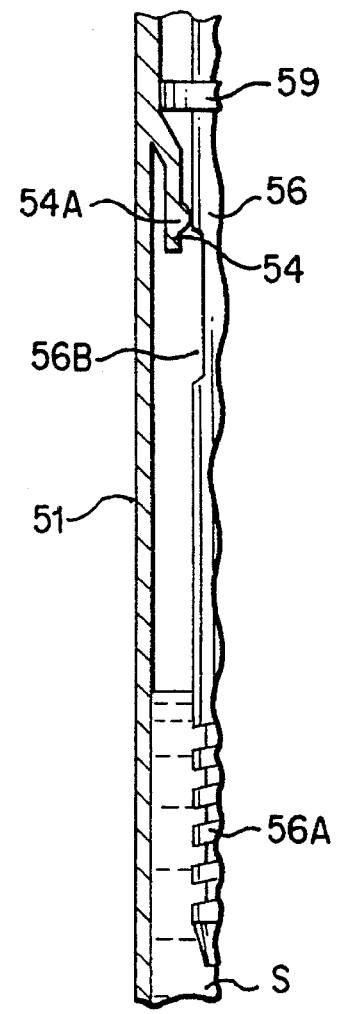
Figure 15:
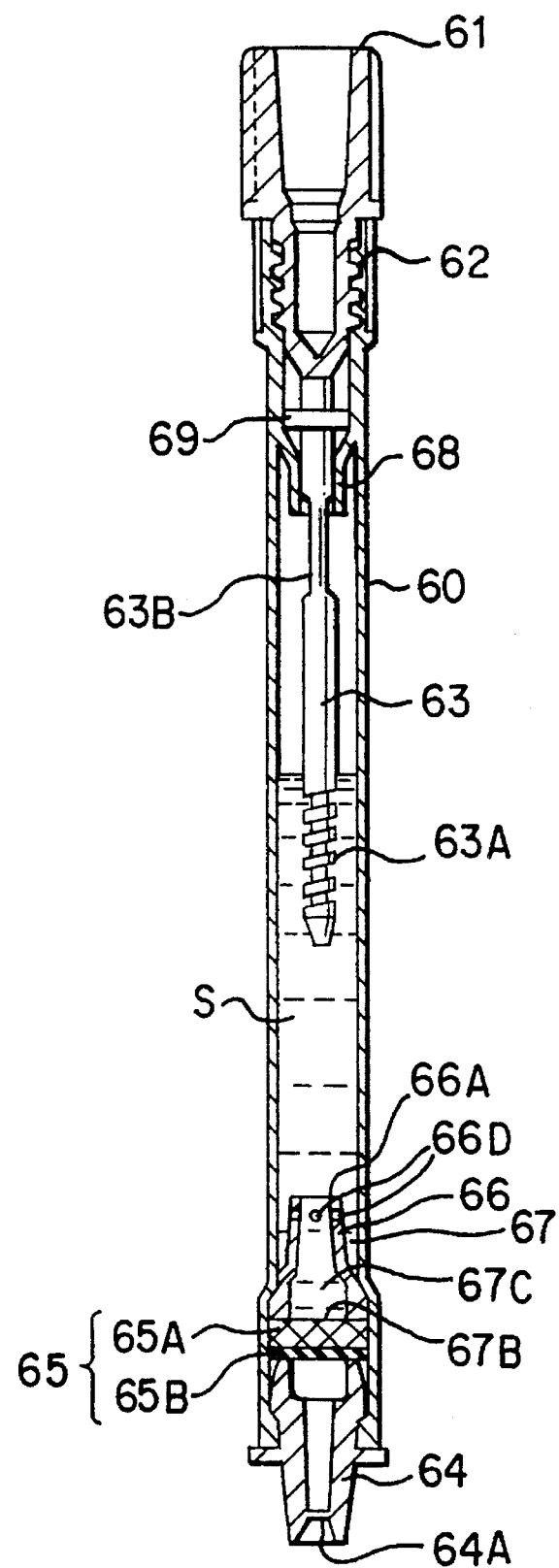
Figure 16:
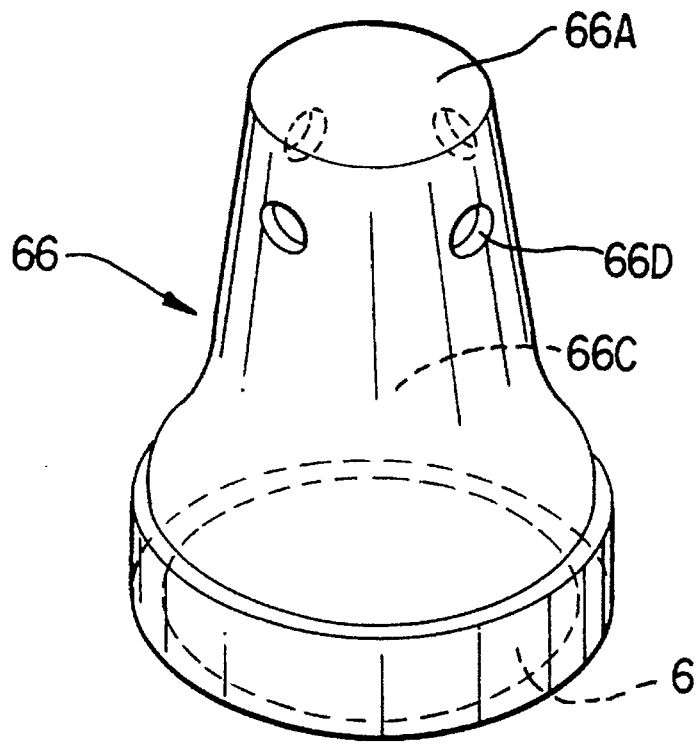
Figure 17:
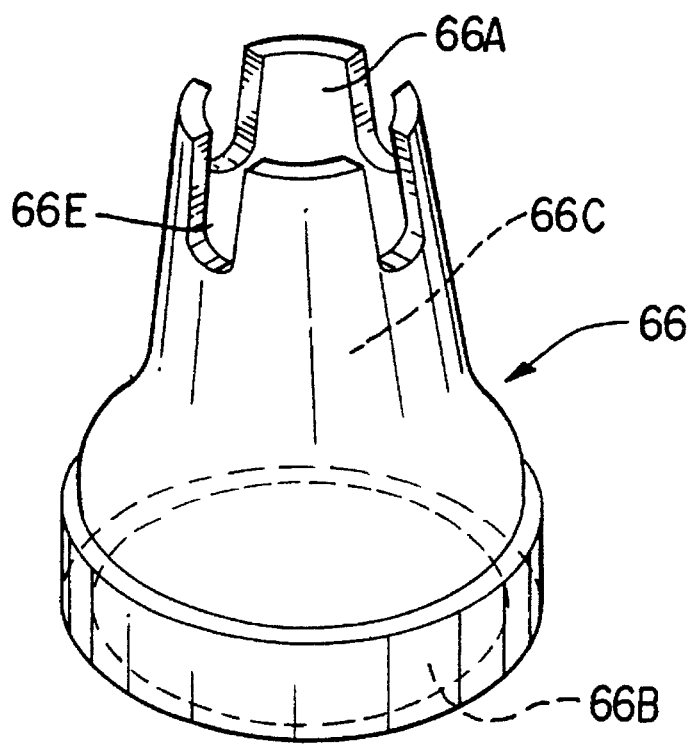
Figure 18:
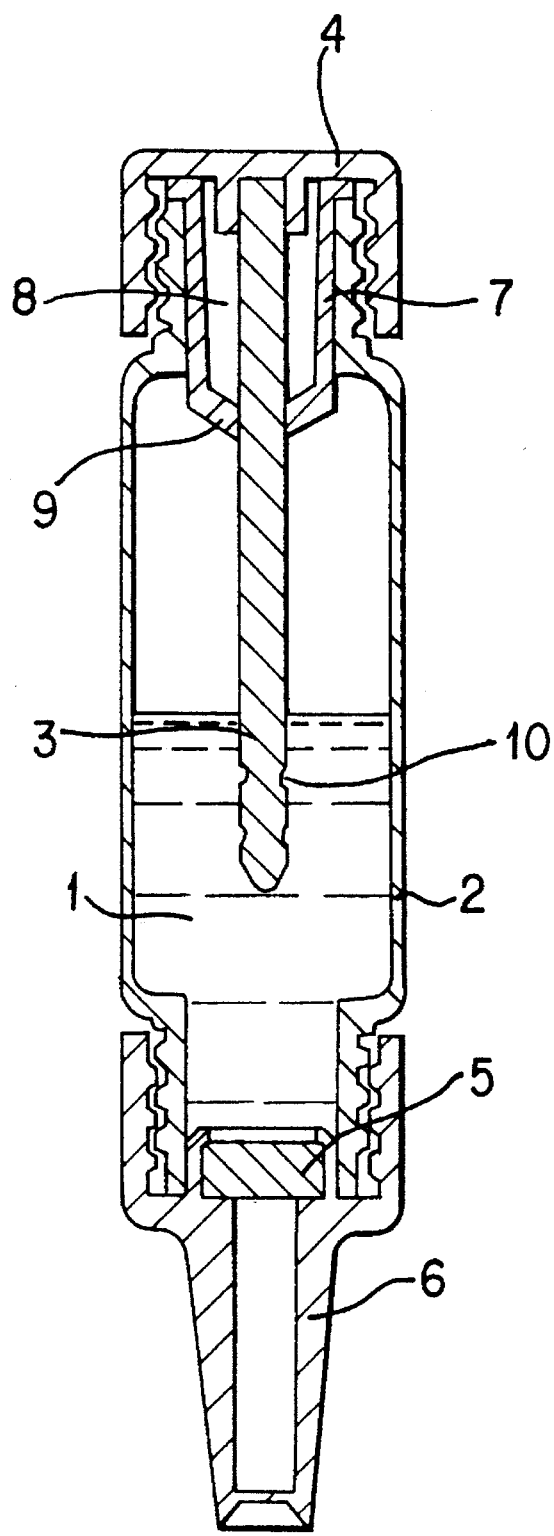
Figure 19:
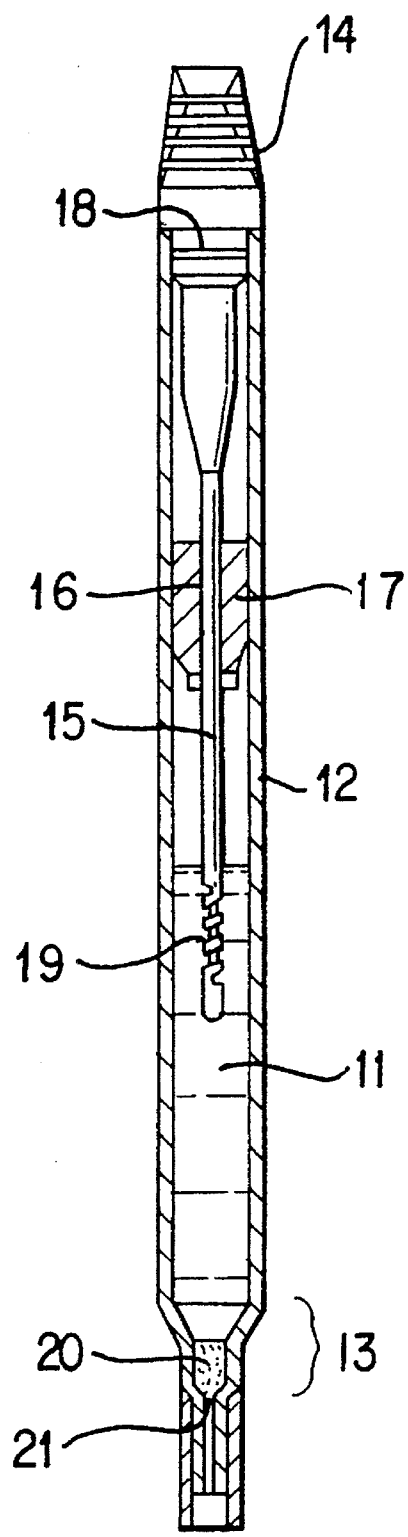

FIG. 9 is an enlarged view showing the vicinity of the separating wall of a feces-sampling transport container according to Embodiment 7 of the present invention;

FIG. 10 is a longitudinal section showing a feces-sampling transport container according to Embodiment 8 of the present invention;

FIG. 11 is an explanatory view showing the engaging portion between the separating wall and the sampling rod of the feces-sampling transport container of FIG. 10 in an enlarged scale;

FIG. 12 is an explanatory view showing the positional relation between the separating wall and the sampling rod of the feces-sampling transport container shown in FIG. 10;

FIG. 13 is an explanatory view showing the positional relation between the separating wall and the sampling rod of the feces-sampling transport container shown in FIG. 10;

FIG. 14 is an explanatory view showing the positional relation between the separating wall and the sampling rod of the feces-sampling transport container shown in FIG. 10;

FIG. 15 is a longitudinal section showing a feces-sampling transport container according to Embodiment 9 of the present invention;

FIG. 16 is a perspective view showing one example of a ring-shaped stopper member in the feces-sampling transport container shown in FIG. 15;

FIG. 17 is a perspective view showing another example of a ring-shaped stopper member in the feces-sampling transport container shown in FIG. 15;

FIG. 18 is an explanatory view showing one example of the feces-sampling container of the prior art; and FIG. 19 is an explanatory view showing one example of the feces-sampling transport container of the prior art.

BEST MODE FOR CARRYING OUT THE INVENTION

The present invention will be described in more detail in the following in connection with its embodiments.

EMBODIMENT 1

Figure 1:
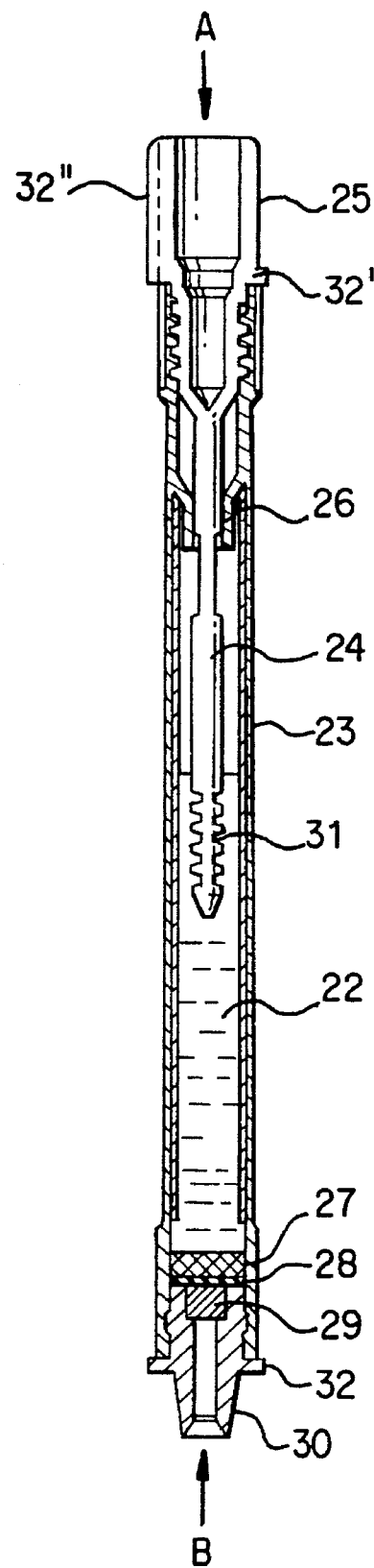
FIG. 1 is an explanatory view showing a feces-sampling transport container according to Embodiment 1 of the present invention.

FIG. 1 shows a feces-sampling transport container according to Embodiment 1 of the present invention. In FIG. 1: reference numeral 22 designates a liquid; numeral 23 a container body; numeral 24 a sampling rod; numeral 25 a cap; numeral 26 a separating wall; numeral 27 a plastic filter; numeral 28 a glass wool filter; numeral 29 a polyurethane sponge filter; numeral 30 a dropping portion; numeral 31 recesses; numeral 32 a flange; numeral 32' a cap flange; and numeral 32" cap knurls. In this Embodiment, the flange 32 is hexagonal. Moreover, the cap 25 is formed with the (hexagonal) cap flange 32' or the (totally three) cap knurls 32". If the container body 23 has its inner wall surface treated with a corona discharge or lithium hydroxide, the inner wall surface has its wettability improved. Hence, this treatment is preferable because the sample or feces can be easily suspended.

Figures 2A, 2B:
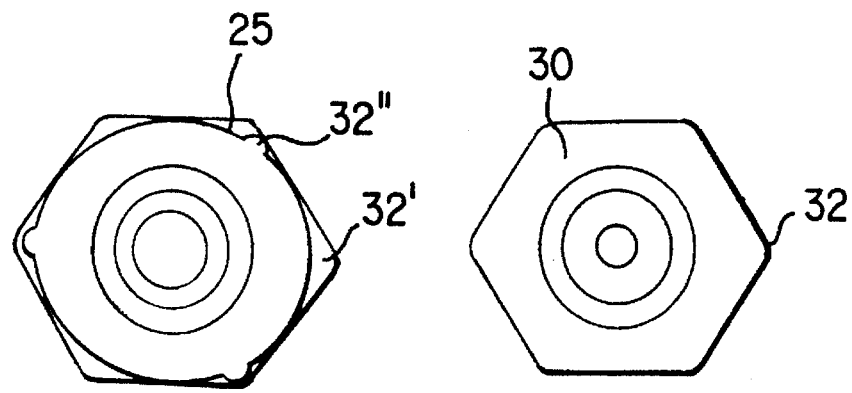
FIG. 2 is a top plan view showing the two end portions of the feces-sampling transport container of FIG. 1, as viewed in the longitudinal direction.

FIG. 2 presents the end faces of the feces-sampling transport container of FIG. 1, as viewed in the longitudinal direction. Specifically, FIG. 2(a) is a top plan view of FIG. 1, as taken in the direction A, and FIG. 2(b) is a top plan view of FIG. 1, as taken in the direction B. Incidentally, FIG. 2(a) shows the two cases in which the cap is formed with the cap flange 32' and the cap knurls 32".

Figure 3:
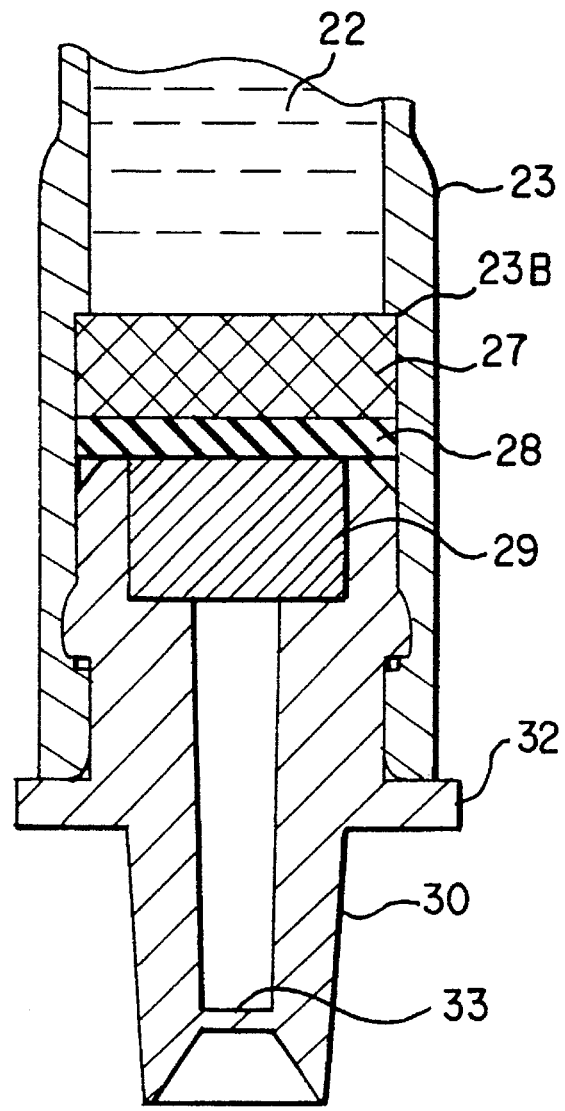
FIG. 3 is an enlarged view showing the vicinity of the dropping portion of the feces-sampling transport container of FIG. 1.

On the other hand, FIG. 3 is an enlarged view showing the vicinity of the dropping portion of the feces-sampling transport container of FIG. 1. For use, a partition 33 is holed or pierced, and the container body 23 is squeezed with fingers. Then, the liquid 22 having the feces suspended therein can be extracted in the form of filtered droplets from the hole of the partition after it has passed through the plastic filter 27 (which engages a stepped portion 23B) the glass wool filter 28 and the polyurethane sponge filter 29 sequentially.

EMBODIMENT 2

Figure 4:
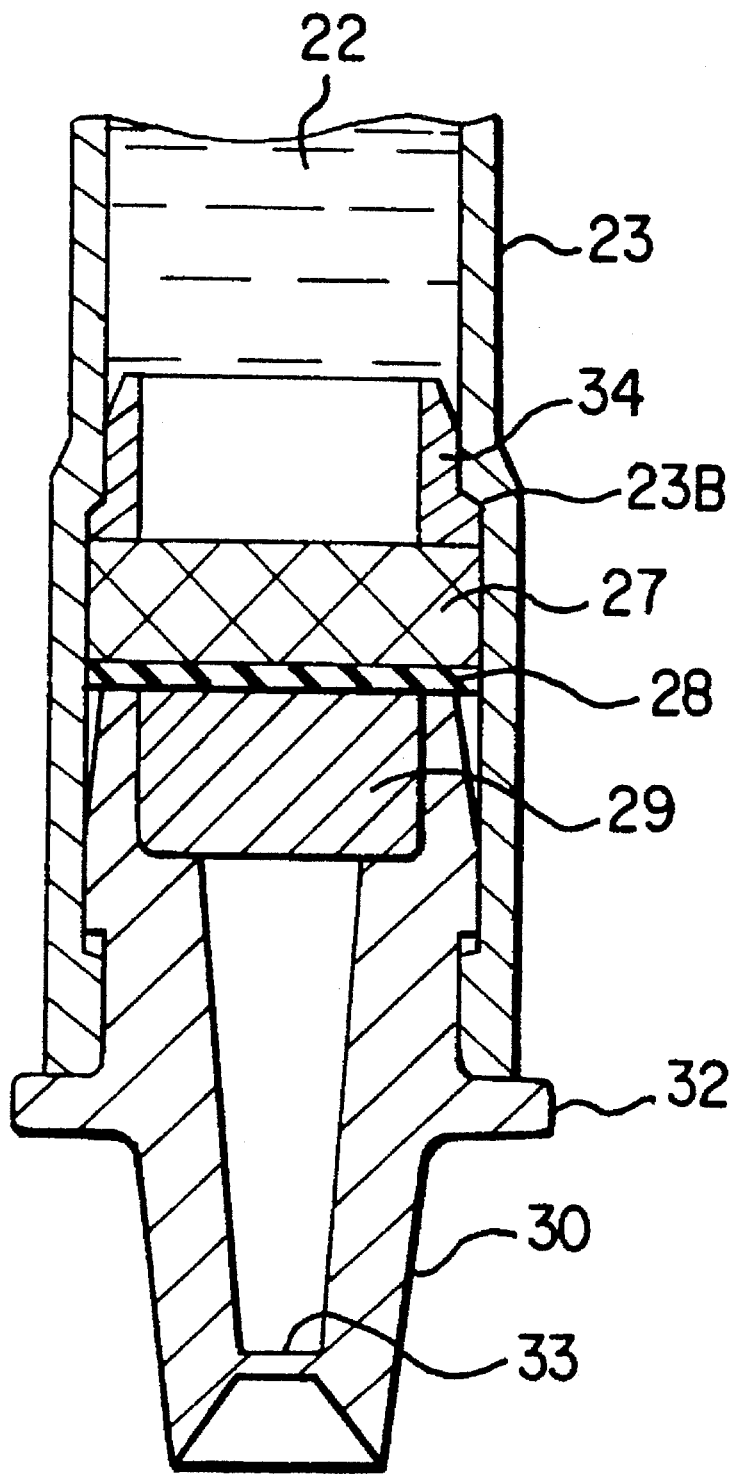
FIG. 4 is an enlarged view showing the vicinity of the dropping portion of a feces-sampling transport container according to Embodiment 2 of the present invention.

FIG. 4 is an enlarged view showing the vicinity of the dropping portion of a fetes-sampling transport container according to Embodiment 2 of the present invention. This Embodiment is identical to the feces-sampling transport container of Embodiment 1 excepting that a stopper ring 34 is disposed over the plastic filter 27. This stopper ring 34 is molded, for example, of a more rigid material than that of the container body 28 into such a predetermined shape as can fit on the stepped portion 23B of the container body 23. In case the container body 28 is manually squeezed for use, it is possible to prevent the plastic filter 27 and the glass wool filter 28 from being deformed.

EMBODIMENT 3

Figure 5:
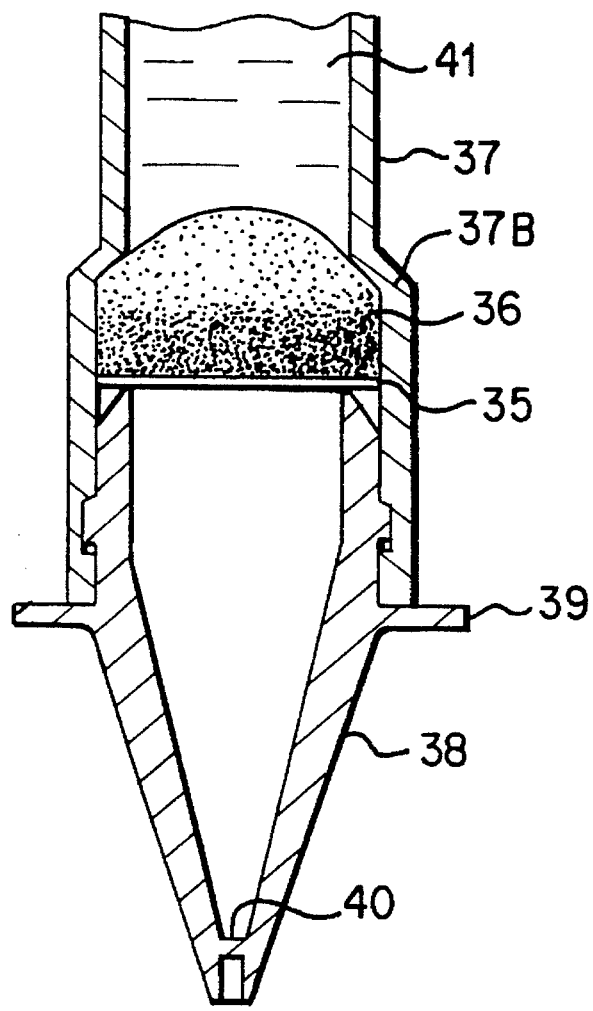
FIG. 5 is an enlarged view showing the vicinity of the dropping portion of a feces-sampling transport container according to Embodiment 3 of the present invention.

FIG. 5 is an enlarged view showing the vicinity of the dropping portion of a feces-sampling transport container according to Embodiment 3 of the present invention. In this Embodiment, a (black) plastic filter 36 is arranged as a pre-filter upstream of a glass wool filter 35 having an average pore diameter of 0.3 μm. The glass wool filter 35 and the malt filter 36 are held between the stepped portion 37B of a container body 37 and a dropping portion 38 (including a hexagonal flange 39 and a partition 40).

Figure 6:
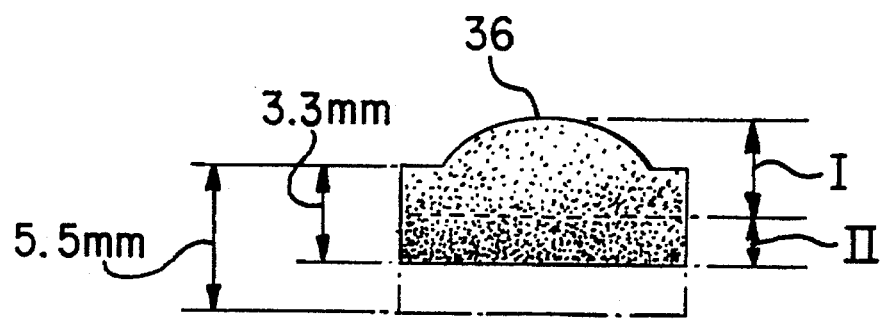
FIG. 6 is an enlarged view showing a malt filter shown in FIG. 5.

FIG. 6 is an enlarged view showing the plastic filter 36. This plastic filter 36 has a thickness of 5.5 mm at its portion excepting the bulging portion and is compressed to a thickness of 3.3 mm by the stepped portion of the container body 37 and the dropping portion 38. In this case, a portion II is compressed more densely than a portion I including the bulging portion and the succeeding portion. For use, therefore, the partition 40 is holed or pierced, and the container body 37 is squeezed with fingers. Then, a liquid 41 having the feces suspended is filtered coarsely through the portion I of the plastic filter 36, intermediately through the portion II of the plastic filter 36 and finely through the glass wool filter 35 so that it can be extracted in the form of filtered droplets from the hole of the partition 40.

EMBODIMENT 4

Figure 7:
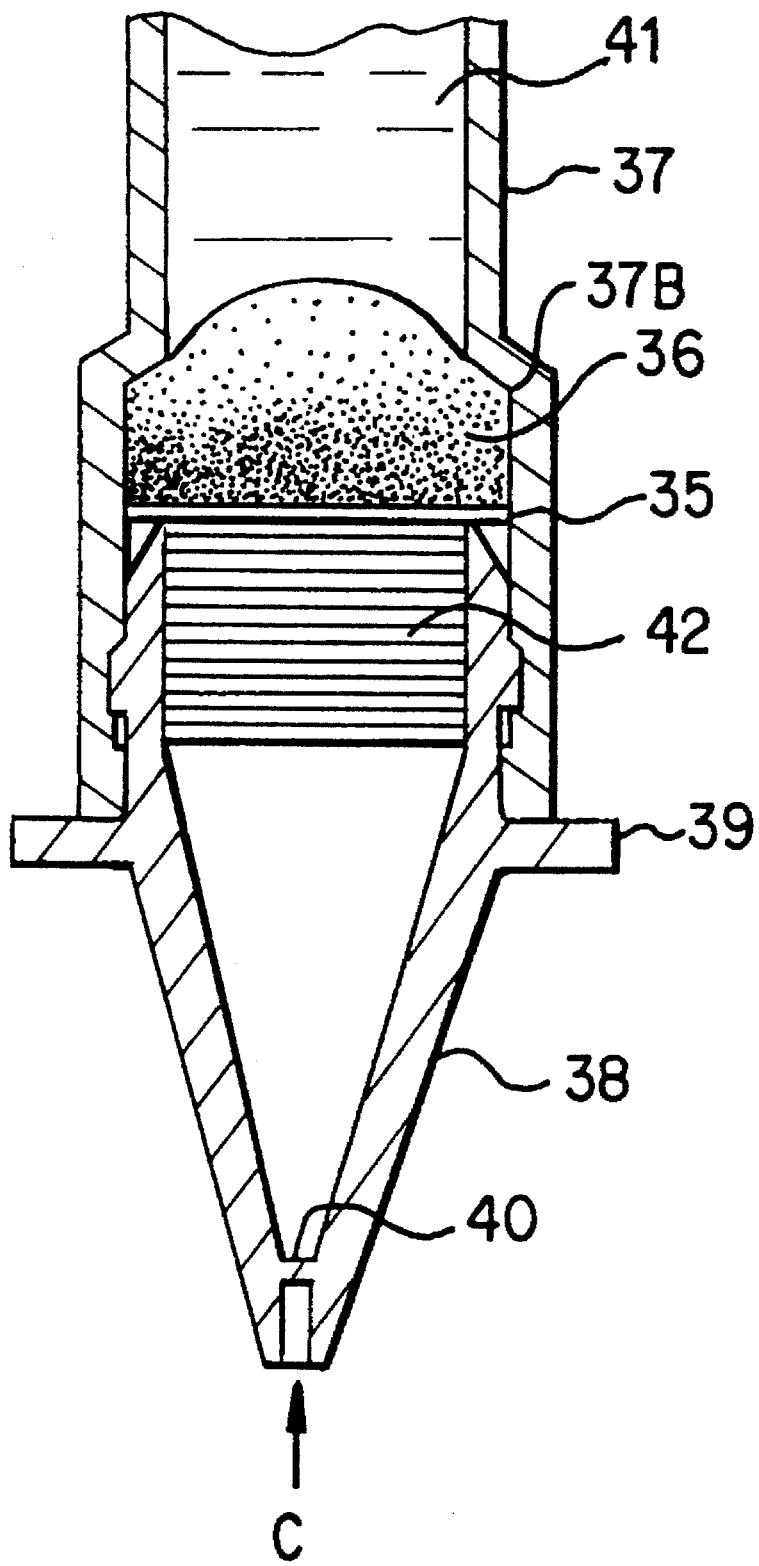
FIG. 7 is an enlarged view showing the vicinity of the dropping portion of a feces-sampling transport container according to Embodiment 4 of the present invention.

FIG. 7 is an enlarged view showing the vicinity of the dropping portion of a feces-sampling transport container according to Embodiment 4 of the present invention. This Embodiment is identical to the feces-sampling transport container of Embodiment 3 excepting that the dropping portion 38 is charged with a polyurethane sponge filter 42. Thanks to this polyurethane sponge filter 42, it is possible to prevent the dispersion of the filtering accuracy, which might otherwise be caused as a result of deformation of the glass wool filter 35, which is located within a stepped portion 37B, when the container body 37 is manually squeezed for use, and the glass wool filter 35 from coming out of position.

EMBODIMENTS 5 & 6

Figure 8:
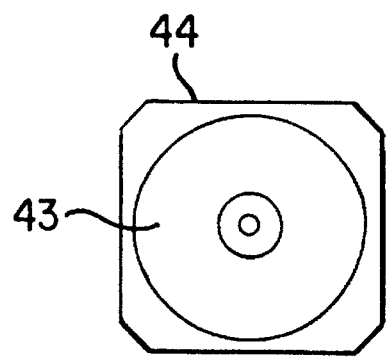
FIG. 8 shows the dropping portions of individual feces-sampling transport containers according to Embodiment 5 and Embodiment 6 of the present invention, as viewed in the direction C of FIG. 7.
Figure 8:
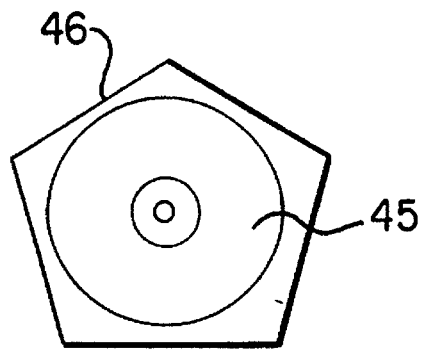

FIG. 8 presents the dropping portions of individual feces-sampling transport containers according to Embodiment 5 and Embodiment 6 of the present invention, as viewed in the direction C of FIG. 7. The feces-sampling transport containers of Embodiments 5 and 6 are identical to the feces-sampling transport container of Embodiment 4 excepting that the flange has different shapes. Specifically, in the feces-sampling transport container of Embodiment 5, a dropping portion 43 is formed with a flange 44 having a chamfered square, as shown in FIG. 8(a). In the feces-sampling transport container of Embodiment 6, on the other hand, a dropping portion 45 is equipped with a pentagonal flange 46, as shown in FIG. 8(b).

EMBODIMENT 7

FIG. 9 is an enlarged view showing the vicinity of the separating wall of a feces-sampling transport container according to Embodiment 7 of the present invention. This Embodiment is identical to the feces-sampling transport container of Embodiment 1 excepting that a separating wall 47 is formed with a bulging portion 48 and that a sampling rod 49 is formed with a recessed portion 50. In the feces-sampling transport container of this Embodiment, the bulging portion 48 goes into the recessed portion 50 so that the interference of the separating wall 47 can be sufficiently retained but not reduced due to aging.

EMBODIMENT 8

FIG. 10 shows a feces-sampling transport container according to Embodiment 8 of the present invention. In FIG. 10: reference numeral 51 designates a cylindrical container body; numeral 52 a cap; numeral 53 a screwed portion between the container body 51 and the cap 52; numeral 54 a separating wall disposed concentrically in the inner circumferential wall of the container body 51 and having a center hole; numeral 56 a sampling rod formed integrally with the lower face of the cap 52; numeral 56A a helical groove formed in the leading end of the sampling rod 56 for accommodating a predetermined amount of feces; and numeral 54A a ridge formed on the circumference of the cylindrical wall of the aforementioned separating wall 54 such that it can hermetically engage with the circumference of the sampling rod 56. Reference numeral 57 designates a filter which is composed of a plastic filter 57A and a glass wool filter 57B. Numeral 55 designates a dropping portion; numeral 55A a thinned portion formed in the dropping portion; numeral 58 a filter stopping stopper ring; and numeral 59 a stopper for regulating the lowermost position of the sampling rod 56. The aforementioned sampling rod 56 is formed, in its outer circumference corresponding to the ridge 54A of the separating wall 54, with a notched groove 56B as a recess extending in the axial direction. The notched groove 56B has a larger axial length than that of the entirety of the separating wall 54 including the ridge 54A.

FIG. 11 is an enlarged longitudinal section showing the vicinity of the separating wall 54 of the feces-sampling transport container of Embodiment 8. In this Embodiment, the separating wall 54 is molded as a concentric cylindrical wall integrally with the inner circumference of the container body 51 of a synthetic resin and has its central portion formed with a center hole for allowing the sampling rod 56 to fit therein and pass therethrough. Moreover, the aforementioned cylindrical wall is formed on its inner circumference with the scraping ridge 54A. On the other hand, the sampling rod 56 is formed in its outer circumference with the notched groove 56B which extends in the axial direction to act as an air communication recess. This axial length is made slightly larger than that of the separating wall 54 so that an air communication passage may be formed without fall in the container body 51 between the spaces above and below the separating wall 54 when the sampling rod 56 takes a later-described insertion position, as shown in FIG. 13. Moreover, the notched groove 56B has its radial depth set such that the radial displacement of the ridge 54A of the separating wall 54, if caused in the notched groove 56B by the reaction at the engaging time, can be sufficiently accommodated.

In the feces-sampling transport container of this Embodiment, the sampling rod 56 having sampled the feces in the helical groove 56A at its leading end is inserted through the center hole of the separating wall 54 into the container body 51 which has been charged in advance with an aqueous solution of 2.0 cc. The feces caught by the leading end portion is rubbed out by the ridge 54A of the separating wall 54 so that a predetermined amount of feces is left in the helical groove 56A.

In the state in which the sampling rod 56 is inserted to the position, as shown in FIG. 12, the sampling rod 56 and the ridge 54A formed on the cylindrical wall of the separating wall 54 are in hermetical sliding contact with each other under the elastic deformation of the separating wall 54 so that the pressure of the space of the container body 51 confining a liquid S below the separating wall 54 rises to a level higher than the atmospheric pressure in accordance with the volume of the portion into which is inserted the sampling rod 56.

As the sampling rod 56 is further inserted from that state to the position, as shown in FIG. 13, its notched groove 56B confronts the ridge 54A of the separating wall 54. Since the notched groove 56B is made longer than the axial length of the ridge 54A of the separating wall 54 and since a sufficient gap is left between the crest of the ridge 54A of the separating wall 54 and the bottom of the notched groove 56B, there is established between the notched groove 56B and ridge 54A an air communication passage, as indicated by arrow P, for providing the communication between the spaces of the container body 51 above and below the separating wall 54. Since, in this position, the container body 51 is not completely screwed on the cap 52, the air in the container body under a super-atmospheric pressure is released to the outside of the feces-sampling container so that the pressure in the container body 51 is lowered to the atmospheric level.

As the cap 52 is then turned along the screwed portion 53 with respect to the container body 51, the sampling rod 56 is further lowered to the position of FIG. 14 by the screwed relation to the container body 51 so that its outer circumference and the ridge 54A on the inner circumference of the separating wall 54 restore their hermetical sliding relation to seal the liquid S completely in the container body 51.

At this time, the sampling rod 56 further protrudes to the screwed extent, but the resultant pressure rise is slight. In this case, the stopper 59 formed on the sampling rod 56 comes into abutment against the upper end of the separating wall 54 thereby to suppress any further downward movement of the sampling rod 56. As a result, there arises no fear that the screwed portion 53 or the separating wall 54 would be deformed or broken even if the cap 52 should be erroneously turned to force the sampling rod 56 excessively into the container body 51.

Since, moreover, the sampling rod 56 is in sliding contact with the cylindrical wall of the separating wall 54 only at the ridge 54A, the sliding resistance when the sampling rod 56 is to be inserted can be reduced to a lower level to remarkably improve the rubbing-off properties of the feces and the sealing properties between the separating wall 54 and the sampling rod 56.

The feces-sampling container thus having the feces suspension sealed in the container body is transported by means of mail to predetermined examination facilities, in which the dropping portion 55 has its thinned portion pierced for examinations by means of needle. Then, the liquid S in the container body 51 is dropped for the examinations to the outside through the filter 57 by squeezing the circumferential wall of the container body 51 made of a flexible synthetic resin.

EMBODIMENT 9

FIG. 15 is a longitudinal section showing a feces-sampling transport container according to Embodiment 9 of the present invention. In FIG. 15: reference numeral 60 designates a cylindrical container body; numeral 61 a cap; numeral 62 a screwed portion between the container body 60 and the cap 61; numeral 63 a sampling rod integrally depending from the lower face of the cap 61; numeral 63A a helical groove formed at the leading end of the sampling rod for accommodating a predetermined amount of feces; numeral 63B an air vent groove formed in the circumference of the sampling rod; numeral 64 a dropping portion disposed in the lower end of the container body 60; and 64A a thinned portion formed in the dropping portion. All of these components are formed by molding a synthetic resin. Numeral 65 designates a filter which is composed of a plastic filter 65A and a glass wool filter 65B. Numeral 66 designates a hollow stopper ring which is concentrically fitted in the container body 60 above the filter 65 for fixing and holding the filter 65 between it and the aforementioned underlying dropping portion 64.

In addition, reference numeral 68 appearing in FIG. 15 designates a separating wall projecting integrally and concentrically with the inner circumferential wall of the container body 60. The aforementioned sampling rod 63 has its outer circumference brought, as it is inserted, into sliding contact with the separating wall 68 so that the feces other than a predetermined amount accommodated in the helical groove 63A is rubbed out. Numeral 69 designates a stopper which is formed on the outer circumference of the sampling rod 63 to regulate the excessive protrusion of the sampling rod being inserted.

The aforementioned stopper ring 66 is formed, as shown in section in FIG. 15 and in perspective view in FIG. 16, to have an upper end portion 66A closed, a lower open end 66B contacting with the filtering face of the filter 65, and an internal inlet portion 66C having a diameter enlarged gradually from the upper end portion 66A to the lower open end 66B. A depositing portion 67 is formed between the outer circumferential wall of the aforementioned stopper ring 66 and the inner circumferential wall of the container body 60.

The stopper ring 66 is formed in its circumferential wall of the upper end portion 66A with a number of through holes 66D acting as inlet holes for providing communication in the radial direction of the container body 60 between the internal inlet portion 66C and the depositing portion 67.

In the feces-sampling container of this Embodiment, the sampling rod 63 having sampled the feces in the helical groove 63A at its leading end is inserted through the center hole of the separating wall 68 into the container body 60 which has been charged in advance with an aqueous solution of 2.0 cc. The feces caught by the leading end portion is rubbed out by the sliding contact of the separating wall 68 with the hole wall so that a predetermined amount of feces is left in the helical groove 63A.

In this case, the stopper 69 formed around the sampling rod 63 abuts against the upper end shoulder portion of the separating wall 68, as it is inserted to a predetermined position with respect to the container body 60 by the screwed portion 62 of the cap 1, thereby to suppress any further downward movement of the sampling rod 63. As a result, there is no fear that the screwed portion 62 or the separating wall 68 would be deformed or broken even if the cap 61 should be erroneously turned to force the sampling rod 63 excessively into the container body 60.

When the helical groove 63A at the leading end of the sampling rod 63 is dipped in the aqueous solution contained in the container body 60, as shown in FIG. 15, the feces held in the helical groove 63A is dissolved and suspended in the aqueous solution to prepare an examination sample (or the liquid S) having a predetermined concentration.

Here, the solid substances suspended in the aqueous solution are gradually settled in the container body 60. However, the stopper ring 66 is closed at its upper end portion 66A so that most of the solid substances are deposited on the bottom of the depositing portion 67 between the outer circumferential wall of the ring 66 and the inner circumferential wall of the container body 60. A portion of the solid substances is dispersed in the suspension in the inlet portion 66C through the through holes 66D in the circumferential wall of the stopper ring 66. Since, however, the solid substances having relatively large specific gravities are hard to disperse in the radial directions while they are being suspended, the solid substances hardly migrate into the inlet portion 66C.

Even if the solid substances should be dispersed in a minute amount into the suspension in the inlet portion 66C, they would migrate over a wide area of the filtering face because the inlet portion 66C is formed to diverge toward the lower open end 66B contacting with the filtering face of the filter 65. As a result, the height (or thickness) of the deposited layer is remarkably reduced as the aforementioned divergence increases.

The feces-sampling container thus having the feces suspension sealed in the container body is transported by means of mail to predetermined examination facilities, in which the dropping portion 55 has its thinned portion pierced for examinations by means of needle. Then, the suspension (or the liquid S) in the container body 60 is dropped for the examinations to the outside from the filter 65 through the dropping portion 64 by squeezing the circumferential wall of the container body 60 made of a flexible synthetic resin.

In this case, most of the solid substances in the suspension is deposited on the bottom of the depositing portion 67, as described above, so that they are hardly left on the filtering face. As a result, the filtering efficiency is excellent and constant independently of the properties of the sample feces so that the dropping amount obtained for the analysis is sufficient as the sample to be analyzed and no substantial dispersion among the individual containers is required.

In order to confirm the effects of the feces-sampling transport container of Embodiment 9 specifically, dropping experiments of the suspension were made on five kinds of such hard-filtration feces so as to deteriorate the filtering efficiency of the filter seriously, according to a procedure similar to that described in connection with Embodiment 9, by using the feces-sampling container of Embodiment 9 equipped with the stopper ring and the feces-sampling transport container of Embodiment 1. The experimental results are tabulated in Table 1 as follows.

TABLE 1

| Hard Filtration Feces | Dropping Tests | | | | |
|---|---|---|---|---|---|
| (Sample No.) | 1 | 2 | 3 | 4 | 5 |
| Embodiment 9 (No. of Droplets) | 9 | 10 | 11 | 11 | 9 |
| Embodiment 1 (No. of Droplets) | 4 | 4 | 7 | 5 | 7 |

It is apparent from the results of Table 1 that the numbers of droplets of the feces-sampling transport container of Embodiment 1 using the stopper ring of the prior art are smaller and are dispersed (although practically sufficient) depending upon the kinds of feces. In the feces-sampling transport container using the stopper ring of Embodiment 9, on the contrary, the numbers of droplets are larger, e.g., 9 to 11 over the samples and are less dispersed.

Incidentally, the shape of the stopper ring should not be limited to that of Embodiment 9 but can be improved and modified in various manners. For example, the stopper ring may be exemplified not only by the structure shown in FIG. 16 but also by the structure in which the upper end portion 66A of the inlet portion 66C is opened to have its circumferential edge toothed with cut-away portions 66E acting as radial inlet holes, as shown in FIG. 17. In this modification, too, similar effects of increasing the droplet number and stabilizing the dropping amount can be achieved by making the area of the lower open end 66B of the stopper ring 66 far larger than the sum of the areas of the upper open end 66A and the cut-away portions 66E (i.e., 66A+66E<⅓×66B).

<Performance Comparison Tests>

The dropping tests of hard-extraction feces were made by using the feces-sampling transport container of the present invention (i.e., the feces-sampling transport container of Embodiment 1 shown in FIG. 1: Invention) and the feces-sampling transport container of the prior art (i.e., the feces-sampling transport container disclosed in Japanese Utility Model Laid-Open No. 140468/1990 shown in FIG. 19: Prior Art). The results are summarized in Table 2.

TABLE 2

| Dropping Test Results of Various Feces Using the Invention and the Prior Art | | | | |
|---|---|---|---|---|
| Feces of Patients (No. of Samples) | 1 | 2 | 3 | 4 |
| Invention (No. of Droplets) | 9 | 6 | 12 | 18 |
| Prior Art (No. of Droplets) | 2 | 2 | 5 | 5 |

As is apparent from Table 2, the Invention has a larger Filtration area than that of the prior art so that its filtering efficiency is drastically improved.

FIELD OF INDUSTRIAL APPLICATION

In the feces-sampling transport container of the present invention, the container body is formed on the inner wall of its other end portion with the stepped portion for retaining the filter so that the filter is fixed by having its two end faces clamped at their outer circumferences by the stepped portion and the end face of the dropping portion. As a result, the filter to be used has a diameter substantially equal to the internal diameter of the container body so that its effective filtration area is large. Thus, the filtration area of the filter is far larger than that of the feces-sampling transport container of the prior art so that the filtering efficiency is drastically improved.

As a result, the feces-sampling transport container of the present invention can extract a sufficient amount of sample for the examinations easily From the suspension through the filter even in case it is applied to the hard-extraction feces.

Moreover, the feces-sampling transport container of the present invention can improve the accuracy and efficiency of the feces examinations partly because it has a convenient usability and can sample the feces easily in a proper amount and partly because it can be so easily transported that it can be sent and/or returned by means of mail such as envelopes.

Still moreover, the feces-sampling transport container of the present invention can be modified in various manners, and its design can be finely modified according to the properties of feces so that the degree of freedom of its design is high and practically convenient.

Especially in the feces-sampling transport container of the present invention, in which the substantial seal portion between the container body and the cap is established between the ridge of the separating wall and the outer circumference of the sampling rod, it is possible to reduce the force for inserting the sampling rod and to improve the rubbing-off properties and sealing properties of feces. Since, moreover, the sampling rod has its outer circumference formed with the recess extended in the axial direction to provide the air passage, that pressure in the space charged with the suspension, which is established by inserting the sampling rod into the container body, can be lowered to the atmospheric level immediately before the end of the insertion process, so that the suspension is prevented from being injected or scattered by the excessive pressure to blow the surrounding when the dropping portion is pierced.

Of the feces-sampling transport container of the present invention, still moreover, the hollow stopper member to be brought into contact with the filtering face of the filter is formed into a concentric shape having a smaller diameter than that of the container body to form the depositing portion between the outer circumferential wall of the stopper member and the inner circumferential wall of the container body for separating and settling the solid substances in the suspension. If this stopper member is shaped to have its radial section increased gradually from the upper end to the lower open end at the filtering face, the thickness (or height) of the solid substances to be deposited on the filtering face is reduced, when the suspension of feces is to be produced in the container body, to improve the filtering efficiency so that the number of droplets can be increased to reduce the dispersion and to stabilize the analyzing sensitivity for the examinations.

Especially in case the inlet portion of the aforementioned stopper member is formed with the inlet holes extending radially through the circumferential wall, most of the solid substances to settle in the suspension are deposited as it is in the depositing portion so that they are hardly dispersed into the suspension in the inlet portion from the radial inlet holes. As a result, the deposition of the solid substances on the filtering face can be remarkably reduced.

We claim:

1. A feces-sampling transport container comprising: a cylindrical container body capable of accommodating a liquid for suspending feces; a cap including a sampling rod equipped at a leading end portion thereof with feces sampling means for sampling the feces and adapted to be inserted in the axial direction into said container body, said cap being capable of sealing one end portion of said container body; a separating wall formed in said container body for partitioning the inside of said container body and for removing an excess of the feces when said sampling rod is inserted; a filter disposed adjacent a second end portion of said container body for filtering the suspension of the feces; and a dropping portion fitted in the second end portion of said container body outside of said filter for dropping the liquid filtered by said filter, wherein said container body is formed on an inner wall face of the second end portion with a stepped portion for retaining said filter, so that said filter has a circumference that is fixed at an outer portion thereof between said stepped portion and an end face of said dropping portion.

2. A feces-sampling transport container according to claim 1, wherein said stepped portion is formed by enlarging the internal diameter of said container body.

3. A feces-sampling transport container according to claim 1, wherein said stepped portion is formed by reducing the internal diameter of said container body.

4. A feces-sampling transport container according to claim 3, wherein said container body has a reduced internal diameter defining a stopper ring.

5. A feces-sampling transport container according to claim 1, wherein said filter is an aseptic filter.

6. A feces-sampling transport container according to claim 1, wherein said filter is formed by laminating at least two kinds of filters.

7. A fetes-sampling transport container according to claim 1, wherein the face of said filter to abut against said stepped portion bulges toward said cap from said stepped portion.

8. A feces-sampling transport container according to claim 1, further comprising a filter disposed in the passage above formed below in said dropping portion for the filtered liquid.

9. A feces-sampling transport container according to claim 1, wherein said dropping portion has a flange extended outward from the outer circumference of said container body for preventing said feces-sampling transport container from rolling.

10. A feces-sampling transport container according to claim 1, wherein said cap is flanged or knurled outward from the outer circumference of said container body for preventing said feces-sampling transport container from rolling.

11. A feces-sampling transport container according to claim 1, wherein said container body has an inner wall face treated chemically to improve wettability.

12. A feces-sampling transport container according to claim 11, wherein said physical/chemical treatment is a physical treatment.

13. A feces-sampling transport container according to claim 12, wherein said physical treatment is carried out by a corona discharge.

14. A feces-sampling transport container according to claim 11, wherein said physical/chemical treatment is a chemical treatment.

15. A feces-sampling transport container according to claim 14, wherein said chemical treatment is carried out with lithium hydroxide.

16. A feces-sampling transport container according to claim 1, wherein said container body contains an anti-fogging agent for improving the wettability of the inner wall face of said container body.

17. A feces-sampling transport container according to claim 1, wherein said separating wall is formed into a cylindrical shape having a through hole at an central portion thereof for inserting said sampling rod, by protruding the inner wall face of said container body inward.

18. A feces-sampling transport container according to claim 17, wherein said through hole has an inner wall face formed into an inward bulging ring portion whereas said sampling rod includes a recessed ring portion corresponding to said bulging ring portion.

19. A feces-sampling transport container according to claim 1, wherein said separating wall includes a circumference with a feces scraping ridge for engaging hermetically with the circumference of said sampling rod, and wherein said sampling rod has a circumference formed with at least one recess which is made axially longer than the scraping ridge of said separating wall and confronts said separating wall, whereby communication is provided between spaces in said container body, which are partitioned by said separating wall, to reduce the pressure in said container body to the atmospheric level before said sampling rod is inserted to a predetermined position in said container body.

20. A feces-sampling transport container according to claim 19, wherein said scraping ridge is formed adjacent a free end portion of said separating wall.

21. A feces-sampling transport container according to claim 19, wherein the recess formed in the circumference of said sampling rod is a notched groove formed in a portion of the circumference of said sampling rod.

22. A feces-sampling transport container according to claim 19, wherein the recess formed in the circumference of said sampling rod is formed into a radially reduced portion by notching the circumference of said.

23. A feces-sampling transport container according to claim 1, further comprising a ring-shaped stopper member fitted in said container body inside of said filter and in contact with the filtering face of said filter for clamping and fixing said filter to said dropping portion, wherein said ring-shaped stopper member includes an inlet portion having an upper open end communicating with the inside of said cylindrical container body and a lower open end to contact with the filtering face of said filter, such that said inlet portion has a radial section area increased gradually from said upper open end to said lower open end, and wherein a depositing portion for at least one of separating and settling at least a portion of the solid substances in the suspension of the feces is formed between the outer circumferential wall of said ring-shaped stopper member and the inner circumferential wall of said cylindrical container body.

24. A feces-sampling transport container according to claim 23, wherein said stopper member has its circumferential wall formed with radially opened inlet holes for providing communication between the inlet portion thereof and said depositing portion.

25. A feces-sampling transport container according to claim 23, wherein said stopper member is formed at the edge portion of said upper open end with tooth-shaped cut-away portions opened in the radial direction to act as inlet holes.

26. A feces-sampling transport container according to claim 23, wherein said stopper member has its upper open end closed and formed in the circumferential wall in the adjacent an upper end portion with a multiplicity of radially opened through holes as inlet holes.

27. A feces-sampling transport container according to claim 23, wherein the sectional area ratio of the upper open end of said stopper member, as taken in the radial direction, to the lower open end is no more than ⅓.

28. A feces-sampling transport container according to claim 1, wherein the surface area of that portion of the surface of said filter opposed to said dropping portion, which contacts with the inside space of said container body, is at least 50% or more than the maximum of the sectional area of said container body, as taken normal to the axial direction.

* * * * *